United States Patent [19]
Osborne et al.

[11] Patent Number: 5,834,495
[45] Date of Patent: Nov. 10, 1998

[54] CRYSTALLINE XAMONELINE TARTRATE

[75] Inventors: Linda Marie Osborne, Indianapolis; Lisa Ann Shipley, Fishers, both of Ind.; Svend Treppendahl, Virum; Torben G. Petersen, Lyngby, both of Denmark

[73] Assignee: Novo Nordisk A/S Novo Alle, Bagsvaerd, Denmark

[21] Appl. No.: 756,835

[22] Filed: Nov. 26, 1996

Related U.S. Application Data

[63] Continuation of Ser. No. 526,605, Sep. 11, 1995, abandoned, which is a continuation of Ser. No. 285,600, Aug. 3, 1994, abandoned, which is a continuation of Ser. No. 72,572, Jun. 4, 1993, abandoned.

[51] Int. Cl.$^6$ ........................ A61K 31/445; C07D 417/04
[52] U.S. Cl. ..................... 514/342; 514/340; 546/276; 546/277
[58] Field of Search ........................ 546/276, 277; 514/340, 342

[56] References Cited

U.S. PATENT DOCUMENTS

| | | | |
|---|---|---|---|
| 5,041,455 | 8/1991 | Sauerberg | 514/342 |
| 5,043,345 | 8/1991 | Sauerberg | 514/342 |
| 5,260,311 | 11/1993 | Sauerberg | 514/342 |
| 5,264,444 | 11/1993 | Sauerberg | 514/342 |

OTHER PUBLICATIONS

Sauerberg et al., J. Med. Chem., vol. 35, pp. 2274–2283 (1992).

Berger et al "Pharmaceutical Salts" J. Pharm. Sci. 66(1) 1–19 (1977).

Hamilton et al., Journal of Chromatography, 613 (1993) pp. 365–270.

Levine et al., Life Science, vol. 52, Nos. 5/6 (1993).

*Primary Examiner*—Ceila Chang
*Attorney, Agent, or Firm*—Steve T. Zelson; Elias J. Lambiris

[57] ABSTRACT

The invention provides crystalline 3-(4-hexyloxy-1,2,5-thiadiazol-3-yl)-1,2,5,6-tetrahydro-1-methylpyridine (+) L-hydrogentartrate, its preparation and use as a therapeutic agent.

5 Claims, No Drawings

CRYSTALLINE XAMONELINE TARTRATE

This application is a continuation of application Ser. No. 08/526,605, filed Sep. 11, 1995, now abandoned, which is a continuation of application Ser. No. 08/285,600, filed Aug. 3, 1994, now abandoned, which is a continuation of application Ser. No. 08/072,572, filed Jun. 4, 1993, now abandoned, the contents of which are incorporated herein by reference.

This invention relates to crystalline 3-(4-hexyloxy-1,2,5-thiadiazol-3-yl)-1,2,5,6-tetrahydro-1-methylpyridine (+) L-hydrogentartrate herein referred to as Xamoneline tartrate, its preparation and use as a therapeutic agent.

U.S. Pat. No. 5,043,345 discloses a class of compounds that are muscarinic cholinergic agonists and thus of therapeutic use as stimulants of cognitive functions especially in the treatment of Alzheimer's disease.

In Example 9 of U.S. Pat. No. 5,043,345 the preparation of 3-(4-hexyloxy-1,2,5-thiadiazol-3-yl)-1,2,5,6-tetrahydro-1-methylpyridine of formula I is described:

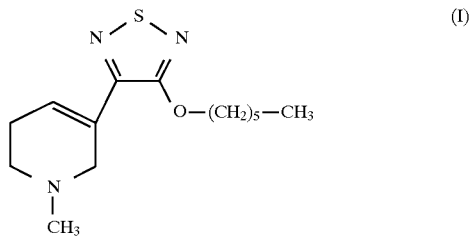

In this specification the compound of formula I is referred to as Xamoneline.

Because of its basicity, it is preferred that Xamoneline is used as a therapeutic agent in the form of an acid addition salt. In Example 9 of U.S. Pat. No. 5,043,345 Xamoneline is obtained as the free base and then converted to its oxalic acid salt.

However, an oxalic acid salt is pharmaceutically undesirable because of the potential for adverse effects on patient kidney function, (J. Pharm. Sci. 1977, 66 (1), 1–19). Oxalic acid salts are particularly undesirable for use in treatment of the elderly.

Furthermore, for commercial use it is important to have a physiologically acceptable salt with good bioavailability, good handling properties, and reproducible crystalline form.

It has now been discovered that out of a series of twelve pharmaceutically acceptable acids, surprisingly, only Xamoneline tartrate has the above described desired properties.

Accordingly, the present invention provides crystalline Xamoneline tartrate as a novel material, in particular in pharmaceutically acceptable form.

The present invention also provides a pharmaceutical composition comprising crystalline Xamoneline tartrate which comprises crystalline Xamoneline tartrate and a pharmaceutically acceptable carrier.

The compositions of this invention are usually adapted for oral administration, but formulations for dissolution for parenteral administration are also within the scope of this invention.

The composition is usually presented as a unit dose composition containing from 1 to 200 mg, more usually from 2 to 100 mg, for example 2 to 50 mg such as 2, 4, 8, 10, 20, 25 or 30 mg. Such composition is normally taken from 1 to 6 times daily, for example 2, 3 or 4 times daily so that the total amount of active agent administered is within the range 4 to 400 mg.

Preferred unit dosage forms include tablets or capsules.

The composition of this invention may be formulated by conventional methods of admixture such as blending, filling and compressing.

Suitable carriers for use in this invention include a diluent, a binder, a disintegrant, a colouring agent, a flavouring agent and/or a preservative. These agents may be utilized in conventional manner, for example in a manner similar to that already used for clinically used agents for treating Alzheimer's disease.

The invention also provides a method of treatment of Alzheimer's disease in mammals including humans which method comprises administering an effective amount of pharmaceutically acceptable crystalline Xamoneline tartrate.

The invention further provides pharmaceutically acceptable crystalline Xamoneline tartrate for use in the treatment of Alzheimer's disease.

Xamoneline tartrate was synthesized, purified and crystallized as described in the following example.

EXAMPLE 1

3-(4-Hexyloxy-1,2,5-thiadiazol-3-yl)-1,2,5,6-tetrahydro-1-methylpyridine (+) L-hydrogentartrate (Xamoneline tartrate)

To a stirred solution of 3-(4-hexyloxy-1,2,5-thiadiazol-3-yl)-1-methylpyridinium iodide (1.00 kg, 2.47 mol) (U.S. Pat. No. 5,043,345) in methanol (4 l) under nitrogen a solution of sodium borohydride (113 g, 2.99 mol) in 0.1N sodium hydroxide (500 ml) was added over 3 h at 0°–5° C. The reaction mixture was stirred for another 30 min. before neutralization with 4N hydrochloric acid (800 ml). The pH was adjusted between 7 and 8 and water (8 l) was added. The mixture was extracted with methylene chloride (2×2 l). The combined organic phases were washed with water and evaporated to give the free base of the title compound in 700 g yield. The residue was dissolved in 2-propanol (2.5 l) and fumaric acid (290 g, 2.50 mol) was added. The mixture was heated to a clear solution, whereafter acetone (2.5 l) was added. The stirred solution was cooled to 5°–10° C. and the precipitated fumarate salt was collected by filtration.

The precipitate (1 kg, 2.52 mol) was suspended in methylene chloride (4 l) and water (2 l) and a sodium hydroxide solution (560 ml, 27.65%, 5.04 mol) was added. The reaction mixture was stirred until a clear solution was obtained, then the methylene chloride phase was separated and washed twice with water (2 l). The organic phase was filtered and evaporated to give the free base of the title compound as an oil. This oil was dissolved in 2-propanol (5 l) and (+) L-tartaric acid (416 g, 2.77 mol) was added. The mixture was heated until a clear solution was obtained. The solution was slowly cooled under stirring to 5°–10° C. and the precipitate was collected by filtration and dried to give the desired product in 980 g (90%) yield. Recrystallization from warm (80° C.) 2-propanol (5 l) added activated carbon (10 g) gave after filtration and cooling to 5°–10° C. pure crystals of the title compound. Crystals were collected by filtration and dried at 40° C. to give 900 g (90%). M.p. 95.5° C. (DSC).

$^1$H-NMR (CD$_3$OD, TMS): δ7.3 (1H, t), 4.9 (4H, s), 4.5 (2H, t), 4.4 (2H, s), 4.2 (2H, s), 3.4 (2H, t), 3.3 (CH$_3$OD), 3.0 (3H, s), 2.7 (2H, q), 1.9 (2H, m), 1.5 (2H, m), 1.4 (4H, m), 0.9 (3H, t).

$^{13}$C-NMR (DMSO-d$_6$, TMS): δ173.8, 162.0, 145.6, 128.1, 126.7, 72.0, 70.9, 52.8, 49.5, 43.7, 30.7, 28.1, 25.0, 24.3, 21.9, 13.8.

MS: 281 (M$^+$).

We claim:

1. A compound which is crystalline 3-(4hexyloxy-1,2,5-thiadiazol-3-yl)-1,2,5,6-tetrahydro-1-methylpyridine (+) L-hydrogen tartrate.

2. A pharmaceutical composition comprising the compound according to claim 1 together with a pharmaceutically acceptable carrier or diluent.

3. The pharmaceutical composition according to claim 2 in the form of an oral dosage unit containing from 1 to 200 mg of the compound.

4. A method of treating cognitive dysfunction caused by Alzheimer's disease in a mammal comprising administering an effective amount of the compound according to claim 1.

5. A method of treating cognitive dysfunction caused by Alzheimer's disease in a mammal comprising administering a pharmaceutical composition according to claim 2.

* * * * *

UNITED STATES PATENT AND TRADEMARK OFFICE
CERTIFICATE OF CORRECTION

PATENT NO. : 5,834,495
DATED : November 10, 1998
INVENTOR(S) : Osborne, et. al.

It is certified that error appears in the above-identified patent and that said Letters Patent is hereby corrected as shown below:

Column 3, line 2 & 3, delete (4hexyloxy-1,2,5-thiadiazol-3-yl)", please insert --(4-hexyloxy-1,2,5-thiadiazol-3-yl)--

Signed and Sealed this

Third Day of October, 2000

Attest:

Q. TODD DICKINSON

*Attesting Officer*   *Director of Patents and Trademarks*